(12) United States Patent
Sevrain

(10) Patent No.: US 8,501,156 B2
(45) Date of Patent: *Aug. 6, 2013

(54) METHOD FOR NON-INVASIVE DETECTION AND TREATMENT OF CEREBRAL ANEURYSMS

(75) Inventor: Lionel C. Sevrain, West Palm Beach, FL (US)

(73) Assignee: Lers Surgical, LLC, West Palm Beach, FL (US)

( * ) Notice: Subject to any disclaimer, the term of this patent is extended or adjusted under 35 U.S.C. 154(b) by 618 days.

This patent is subject to a terminal disclaimer.

(21) Appl. No.: 12/162,424

(22) PCT Filed: Feb. 6, 2007

(86) PCT No.: PCT/US2007/003102
§ 371 (c)(1),
(2), (4) Date: Nov. 6, 2008

(87) PCT Pub. No.: WO2007/092419
PCT Pub. Date: Aug. 16, 2007

(65) Prior Publication Data
US 2009/0068097 A1 Mar. 12, 2009

Related U.S. Application Data

(60) Provisional application No. 60/765,960, filed on Feb. 7, 2006.

(51) Int. Cl.
*A61K 49/00* (2006.01)

(52) U.S. Cl.
USPC ........... 424/9.2; 424/1.11; 424/1.65; 424/9.1; 424/9.6; 206/223; 206/569

(58) Field of Classification Search
USPC ................ 424/1.11, 1.49, 1.65, 130.1, 141.1, 424/142.1, 143.1, 145.1, 146.1, 178.1, 9.1, 424/9.2, 9.6; 206/223, 569, 570
See application file for complete search history.

(56) References Cited

U.S. PATENT DOCUMENTS

| | | | |
|---|---|---|---|
| 7,087,574 B2 * | 8/2006 | Lawrence et al. | 514/13.7 |
| 2004/0043030 A1 * | 3/2004 | Griffiths et al. | 424/178.1 |
| 2005/0255484 A1 * | 11/2005 | Valkirs et al. | 435/6 |

OTHER PUBLICATIONS

Wardlaw et al, Brain, 2000, vol. 123, pp. 205-221.*
The New England Journal of Medicine, 1998, vol. 339, pp. 1725-1733.*
Nakajima et al, Acta Neuropathological, 2000, vol. 100, No. 5, pp. 475-480.*
Weir, J. Neurosurg., 2002, vol. 96, No. 1, pp. 3-42.*
Saito et al, J. Neurosurg., 1977, vol. 47, No. 3, pp. 412-429.*
Torchilin, Targeted Delivery of Imaging Agents, 1995, p. 262.*
International Preliminary Report on Patentability issued Dec. 16, 2008, during the prosecution of International Application No. PCT/US07/003102. Published Dec. 16, 2008.
International Search Report issued Nov. 19, 2008, during the prosecution of International Application No. PCT/US07/03102. Published Jan. 15, 2009.
Written Opinion issued Nov. 19, 2008, during the prosecution of International Application No. PCT/US07/03102. Published Dec. 12, 2008.

* cited by examiner

*Primary Examiner* — D L Jones
(74) *Attorney, Agent, or Firm* — Novak Druce Connolly Bove + Quigg LLP

(57) ABSTRACT

Described herein is a method for non-invasive detection and treatment of intra-cranial aneurysms. Antibodies are provided to specifically react/bind with antigens of the cerebral aneurism wall. The antibodies may be bound to a label and/or to a therapeutic agent for diagnosis and/or for treatment purposes thereof. Intra-cranial aneurysms are thus non-invasively detected before rupture occurs and are specifically treated.

13 Claims, 1 Drawing Sheet

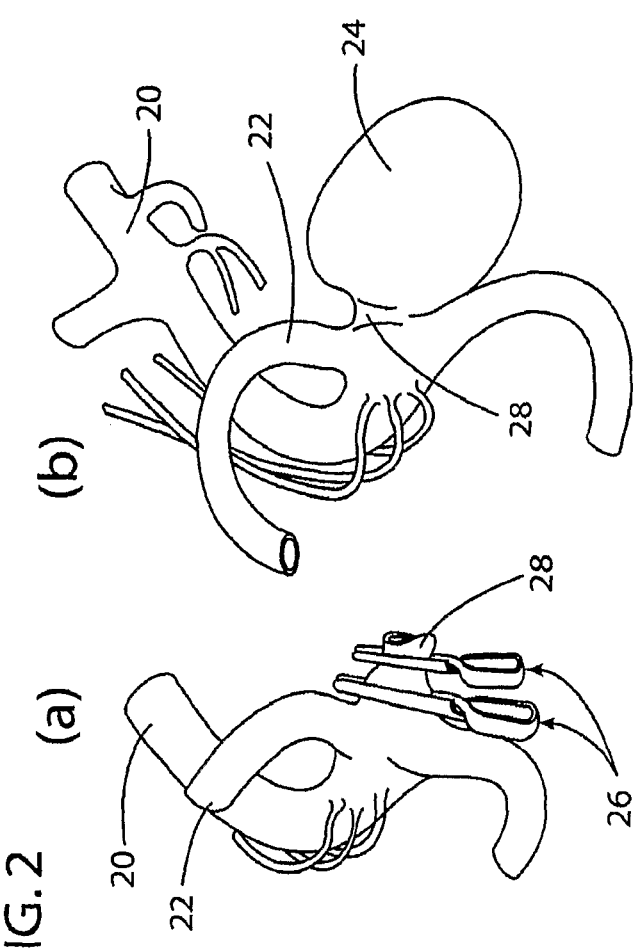
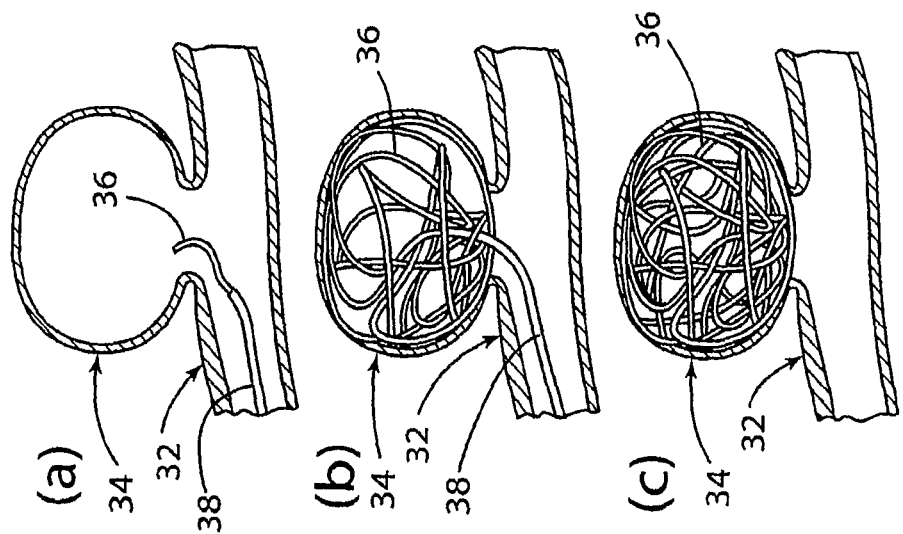
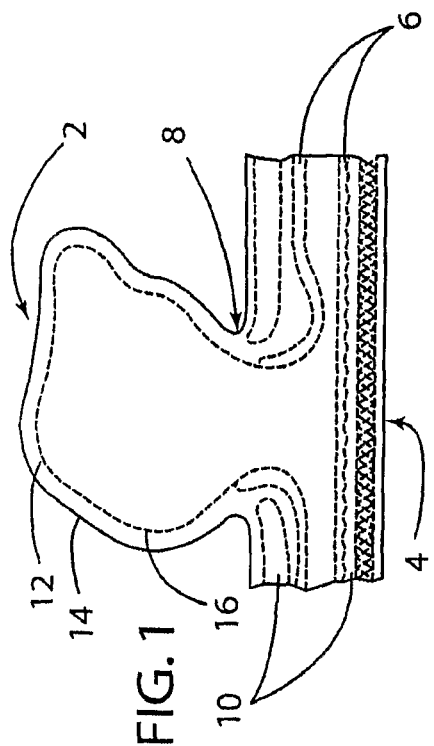

METHOD FOR NON-INVASIVE DETECTION AND TREATMENT OF CEREBRAL ANEURYSMS

CROSS-REFERENCE TO RELATED APPLICATIONS

The present application claims priority to PCT International Patent Application Serial No. PCT/US2007/003102, filed Feb. 6, 2007, and U.S. Provisional Application Ser. No. 60/765,960, filed on Feb. 7, 2006, both of which are herein incorporated by reference in their entirety.

FIELD OF THE INVENTION

The present invention relates to compounds and methods for detecting and/or treating cerebral aneurysms. More specifically, the present invention relates to compounds and methods for the detection and/or treatment of saccular cerebral artery aneurysms.

BACKGROUND OF THE INVENTION

Aneurismal subarachnoid hemorrhage is an increasing problem in the United States, affecting approximately 30,000 people every year. Despite advances in the neurosurgical field, approximately 50% of patients die within the first month after hemorrhage. In fact, most of them die even before reaching the hospital.

The management of cerebral aneurysms raises significant issues both at the diagnostic level and at the therapeutic level. For example, since no selection criteria exists and since their current diagnosis means are expensive and invasive (e.g., 4-axle digital subtraction angiography), no mass detection has yet been considered.

The rate of mortality and morbidity associated with treatment of aneurysms is also significant. For example, surgical clipping or endovascular coiling is responsible for 15% of the morbidity and mortality rate. Recurrence is not insignificant either with approximately 2.2% at 10 years and 9.0% at 20 years after successfully neck clipping.

Most of intracranial aneurysms are clinically quiescent until they rupture. The rate of rupture varies between 0.05% (*International Study of Unruptured Intracranial Aneurysms*) and 2.3% per year. After hemorrhage, the risk of rebleeding is about 40% for the first two months, then 3% per year after the sixth month. The devastating effects of aneurysm rupture advocates preventive treatment and/or diagnosis of unruptured aneurysms.

The most common cerebral aneurysm has the saccular form, a balloon-like distension of a major brain artery occurring at (or near) the apex of arterial forks. It is frequently (around 90%) located on the anterior part of the circle of Willis. Its prevalence varies from 1% to 8% on autopsy series.

Traditionally, craniotomy with aneurismal clipping has been employed to manage these patients, but endovascular embolization is moving to the forefront of treatment.

Surgical clipping of cerebral aneurysms involves the removal of a section of the skull, spreading of the brain tissue to reach the aneurysm and placement of a tiny metal clip across the neck of the aneurysm. Such procedure allows to stop blood flow into the aneurysm and to exclude it from the blood stream. After the aneurysm has been clipped, the bone is secured in its original place, and the wound is closed.

Endovascular therapy (e.g., endovascular coiling with Guglielmi detachable coil) is a minimally invasive procedure that accesses the treatment area from within the blood vessel. In the case of aneurysms, this treatment is called coil embolization, or "coiling". In contrast to surgery, endovascular coiling does not require open surgery. Instead, physicians use real-time X-ray technology, called fluoroscopic imaging, to visualize the patient's vascular system and treat the disease from inside the blood vessel.

Endovascular treatment of brain aneurysms involves insertion of a catheter (small plastic tube) into the femoral artery in the patient's leg and navigating it through the vascular system, into the head and into the aneurysm. Tiny platinum coils are threaded through the catheter and deployed into the aneurysm, blocking blood flow into the aneurysm and preventing rupture. The coils are made of platinum so that they can be visible via X-ray and be flexible enough to conform to the aneurysm shape. This endovascular coiling, or filling of the aneurysm is called embolization and can be performed under general anesthesia or light sedation. More than 125,000 patients worldwide have been treated with detachable platinum coils.

The International Subarachnoid Aneurysm Trial (ISAT), a multi-center prospective randomized clinical trial has been performed for the purpose of comparing surgical clipping and endovascular coiling of ruptured aneurysm.

The study found that, in patients equally suited for both treatment options, endovascular coiling treatment was associated with substantially better patient outcomes than surgery in terms of survival free of disability at one year. The relative risk of death or significant disability at one year for patients treated with coils was 22.6 percent lower than in surgically-treated patients. However, the long-term follow-up will be essential to assess the durability of the substantial early advantage of endovascular coiling over conventional neurosurgical clipping for the treatment of brain aneurysms.

Although no multi-center randomized clinical trial comparing endovascular coiling and surgical treatment of unruptured aneurysms has yet been conducted for the treatment of unruptured aneurysm, retrospective analyses have found that endovascular coiling is associated with less risk of bad outcomes, shorter hospital stays and shorter recovery times than surgery.

In order to improve diagnosis and treatment, current research is performed to elucidate the pathogenesis of cerebral aneurism. A better understanding of the molecular mechanisms involved in the pathogenesis of cerebral aneurism will help to develop medical treatment.

Various hypotheses have been proposed regarding the developmental mechanisms of Saccular Cerebral Artery Aneurysms (SCAAs) such as the medial defect theory, the elastic lamellar theory, degenerative theory, congenital theories, and others. With the recent development of animal model of the disease, it has been possible to study early aneurismal changes and to elucidate the mechanisms of aneurysm formation and development. Studies have showed that hemodynamic stress induces the development of cerebral aneurysms causing degenerative changes of the endothelium, the elastic lamina and the medial smooth muscle cells at specific site on the arterial bifurcation. The anterior cerebral artery/olfactory artery (ACA/OA) junction is one of the favorite sites of aneurysm development. Its normal structure and changes due to aneurysm development have been widely studied. The apex of a normal ACA/OA junction consists of normal arterial components (endothelial cells, internal elastic lamina, medial smooth muscle cells, and thin adventitial fibrous connective tissue). In the apical region, there is an intimal protrusion called pad consistently located near the apex on the distal side of the ACA. This pad is composed of spindle-shaped cells similar to the medial smooth muscle cells, rich in interstitial tissue. Under and just distal to the intimal pad on the side of the ACA, the internal elastic lamina is thinned and fragmented. The initial changes of aneurysms are localized almost exclusively at the intimal pad and its neighboring distal portion. Internal elastic lamina shows various degenerative changes and disappearance. Different studies have reported severe changes in endothelium. Nagata et al. examined by scanning electron microscopy the luminal surface of the cerebral aneurysms. They noticed some variations in the shape of the endothelial cells from fusiform to polygonal. Some of them showed balloon-like protrusions. Crater-like depressions on the endothelial surface and small holes and enlarged gaps at the junction of the endothelial cells were frequently observed. Gap formation at the junctions between the endothelial cells was one of the most obvious changes on the luminal surface of the aneurysms. Kojima et al. studying various stages of early aneurismal changes reported alterations of the endothelium developing just distal to intimal pad. Degenerated cells with balloons and craters were observed intermingled with regenerated endothelial cells. Interendothelial gaps were also seen. They concluded that some hemodynamic stress, possibly turbulent flow or secondary flow may injure the endothelial cells located distal to the pad, and such injured endothelial cells in turn develop saccular cerebral aneurysms. Stehbens also described severe alterations of the endothelium and subendothelial tissues caused by hemodynamic stress. Kim et al. studied aneurismal changes in experimental monkeys and found endothelial injury. They suggested that aneurismal changes are initiated by degenerative changes in the endothelium, which are followed by alterations in the underlying elastic lamina and, in turn, in the medial layer.

Hazama et al. showed that early aneurismal changes consist in degenerative changes of the Internal Elastic Lamina (I.E.L) at the intimal pad and the neighboring area distal to the pad associated to regressive changes of medial smooth muscle layer. Kim et al. also reported degenerative changes of the I.E.L and medial smooth muscle layer. Morimoto et al. found that the characteristic of SCAA formation in a mouse model was thinning of medial smooth muscle layer and disappearance of the I.E.L. Kondo et al. found that the histological features of aneurismal changes were thinning of the medial layer accompanied by fragmentation or disappearance of internal elastic lamina with wall dilatation. They noted a decreased number of SMCs in the medial layer due to apoptosis. They concluded that the death of medial SMCs through apoptosis plays an important role in aneurysm formation. Frosen et al. found different histological types of saccular cerebral artery aneurysms (SCAAs). Lack of elastic laminas was a common feature in the SCAAs studied. Type A was characterized by endothelialized wall with linearly organized SMC, type B by thickened wall with disorganized SMC, type C by hypocellular wall with either myo-intimal proliferation or thrombosis, type D by an extremely thin thrombosis-lined hypocellular wall.

The precise molecular mechanisms involved in the pathogenesis of cerebral aneurysms have not yet been conclusively identified. Hemodynamic stress has been shown in many investigations to be the major cause of various degenerative changes in SCAA formation. This hemodynamic stress might induce a complex, multifactorial remodeling through a variety of mediators and pathways. Recent studies have reported the role of nitric oxide in the development of SCAA. Inducible NO synthase (iNOS) was induced in response to hemodynamic stress and NO synthesized by iNOS serves to damage the arterial wall and lead to aneurysm formation. Other molecular mechanisms such as active expressions of matrix metalloproteinases, apoptosis of medial smooth muscle cells have been shown associated with SCAA. The role of elastase in the degradation of I.E.L in early aneurismal lesions has also been discussed. Nagata et al. reported that in experimental aneurysms many leukocytes were present adhering to the inter endothelial gaps, which may represent the participation of leukocytes in degradation of the I.E.L. Cajander and Hassler also found extracellular lysosome-like granules closely connected to the disintegrated elastic lamella in the mouths of aneurysms and hypothesized that discharged leukocyte granules containing elastase help to destroy the elastic lamella. Enhanced activity of elastase in the arterial wall may also participate in the degenerative changes of the internal elastic lamina, as in the case of hypertension It is an object of the present invention to provide a method for non-invasive diagnosis and treatment of intra-cranial aneurysms

SUMMARY OF THE INVENTION

It has been suggested that an early sign of cerebral aneurysm (intra-cranial aneurysm) formation is the appearance of gaps between endothelial cells. These gaps render the subendothelial component of the brain artery accessible from the bloodstream.

As the aneurysm formation progresses the degenerative changes in the endothelium may be followed by alterations in the underlying elastic lamina and/or, in turn, in the medial layer and as such these components become exposed.

The present invention relates in one aspect thereof to a compound for targeting or binding a subendothelial component of an artery from the bloodstream.

In an additional aspect, the present invention relates to a pharmaceutical composition comprising a compound for targeting a subendothelial component of an artery and a pharmaceutically acceptable carrier.

More specifically, the compound may target, for example, an antigen which may become accessible from the bloodstream once an endothelial cell layer of a cerebral aneurysm becomes altered. Therefore the compound of the present invention may allow for the targeting of a subendothelial component which may preferably be accessible only upon formation of an aneurysm or once an aneurysm is formed.

In accordance with an embodiment of the invention, the compound may be used for targeting an antigen present in at least one of a tunica intima, an internal elastic lamina, a tunica media and/or a tunica adventitia component of a cerebral artery.

For example, the compound of the present invention may target a surface antigen of a cell, a protein, a proteinic structure present in at least one of internal an elastic lamina, a tunica media and/or a tunica adventitia component of a cerebral artery.

The compound of the present invention may comprise, for example, an antibody.

As used herein the term "antibody" means a polyclonal antibody, a monoclonal antibody, a chimeric antibody, a humanized antibody, a deimmunized antibody, an antigen-binding fragment, an Fab fragment; an F(ab')$_2$ fragment, and Fv fragment, or a synthetic molecule comprising an antigen-binding fragment.

As used herein the term "proteinic structure" means an arrangement comprising at least two proteins (the same or different) in association with one another. For example, a non limitative embodiment of a "proteinic structure" comprises elastic microfibrils.

The antibody may be conjugated (coupled) with a label and/or with a therapeutic agent for detection purposes and/or therapeutic purposes. Conjugates which may comprise an antibody moiety and a label and/or therapeutic moiety are encompassed by the present invention.

The conjugate may be coupled with a macromolecule having a molecular weight such that it may confine the molecule within the vessels, yet allowing it to be cleared from the intravascular compartment.

Macromolecular species may include any molecule, natural or synthetic which as a molecular weight in excess of 1 kilodalton such as but not limited to albumin, transferrin, globulins, pectin, gelatin, dextran, cellulose derivatives.

The conjugate may be coupled with red blood cells (RBC) that may thus confine the conjugate in the vascular compartment The compound of the present invention may be held captive to, yet rapidly cleared from the intravascular space.

The compound of the present invention by being held captive in the vascular compartment may bind subendothelial components of the aneurysm wall via endothelial gaps.

The present invention relates to methods for non-invasively detecting aneurysms before the rupture and/or for non-invasively, securely treating intra-cranial aneurysms.

BRIEF DESCRIPTION OF THE DRAWINGS

In the appended drawings:

FIG. 1 is a schematic representation of an aneurysm,

FIGS. 2(a) and 2(b) are a schematic representation of an aneurysm before (FIG. 2(b)) and after (FIG. 2(a)) surgical clipping and;

FIGS. 3(a) to 3(c) are schematic representations of an endovascular coiling method, showing the progressive introduction of a coil into an aneurysm until the aneurysm is totally blocked from the bloodstream.

DETAILED DESCRIPTION

Example 1

Identification of Aneurysm Specific Antigenic Structures

The arterial wall is composed of a series of layers identified as tunica intima, tunica media and tunica adventitia.

The tunica intima is the innermost layer of an artery. It is made up of one layer of endothelial cells supported by a basement membrane. The endothelial cells are in direct contact with the blood flow. The tunica intima more particularly consists of: (a) a layer of pavement endothelium, the cells of which are polygonal, oval, or fusiform, and have very distinct round or oval nuclei, (b) a basement membrane that is a thin sheet of collagen and glycoproteins The tunica intima is separated from the tunica media by an internal elastic lamina that is made of elastic fibers.

The tunica media is the middle layer of the artery. The tunica media is made up of smooth muscle cells and elastic tissue. It lies between the tunica intima on the inside and the tunica adventitia on the outside.

The tunica adventitia is the outermost layer of a blood vessel, surrounding the tunica media. It is mainly composed of collagen. The collagen serves to anchor the blood vessel to nearby organs, giving it stability.

The basement membrane is a subendothelial connective tissue made of glycoproteins and collagen. The major molecular components are kalinin, nicein, laminins, epiligin, 19DEJ1 antigen, hyaluronic acid, perlecan, thrombospondin, fibronectin, heparan sulfate proteoglycan chondroitin-6-sulfate proteoglycan and collagen IV.

The elastic fibers are bundles of proteins (elastin) found in connective tissue and produced by fibroblasts and smooth muscle cells in arteries. These fibers can stretch up to 1.5 times their length, and snap back to their original length when relaxed. The elastic fiber is formed from the elastic microfibril (consisting of numerous proteins such as microfibrillar-associated glycoproteins, fibrillin, fibullin, and the elastin receptor) and amorphous elastin. Desmosine, isodesmosine, and a number of other polyfunctional proteins crosslinks join surrounding elastin molecules to build an elastin matrix and elastic fiber. These unique crosslinks are responsible for elastin's elasticity.

Some recent works have shown that in an aneurysm (FIG. 1) the endothelial layer is damaged, unmasking underlying components which are not normally present along the vascular tree, and so, these structures are specifically targeted from the bloodstream. FIG. 1 illustrates an aneurysm (2) which has formed in an artery (4). As may be seen for FIG. 1, the internal elastic lamina (6) may be absent at the aneurismal neck (8). The media layer (10) may also cease abruptly proximal to the aneurismal neck (8). The wall (12) of the aneurysm (2) may consist only of a fibrous adventitia (14) and a layer of endothelial cells (16).

Therefore, for the purpose of carrying out the invention, any subendothelial component may be used as a specific target of aneurysm. More particularly, the present invention may be used for targeting molecular structures and/or cellular elements normally present in the sub-endothelial layers of the arterial wall or abnormally present in the sub-endothelial layers of the aneurismal wall. A subendothelial component may include for example, a protein or proteinic structure (e.g., part of an elastic fiber) and/or a cell surface antigen (e.g. of a fibroblast, or a smooth muscle cell). Such component may be for example: collagen, laminin, fibronectin, elastin, elastin microfibrillar-associated proteins, desmosine, isodesmosine, cell surface antigen of smooth muscle cell or fibroblast. Such component may be a component expressed due to the vascular wall pathological response such as elastin degradation products (EDP), elastase, intracellular structural proteins, angiogenetic growth factors such as vascular endothelial growth factor (VEGF), basic fibroblast growth factor (bFGF).

A suitable target (aneurismal marker) for aneurysm detection and/or treatment may thus preferably be accessible from the vascular compartment trough the endothelial defects and located within the subendothelial layer of the vasculature.

Example 2

Generation of Antibodies To Target

An antibody (Ab) able to specifically react/bind with a selected antigen (Ag) may be generated by techniques known in the art or may be purchased from commercial sources.

An antibody may be generated by immunizing an animal with a target of choice. For example, the host animal may be immunized with a protein or proteinic structure and/or a protein fragment so as to induce an immune response prior to extracting serum or cells which are responsible for production of antibodies.

For producing monoclonal antibodies and hybridoma a pathogen free mice (e.g., Balb/c, Swiss Webster, IRC/F1 or C57/black), rats (Sprague Dawley) or Armenian hamsters (for reference, see: Current Protocols in Immunology, John Wiley & Sons, New York, 1991) may be used.

Cells, peptide or purified antigen are emulsified in adjuvant (RIBI, Freuds or TiterMax) and the emulsified antigen is injected intraperitoneally. This is followed by two more intraperitoneal injections of antigen emulsified in adjuvant at 3-4 week intervals. Antibody titer is determined using 50-100 µl of blood obtained from the tail vein or retro-orbital plexus obtained by standard procedures with animal under inhalational anesthesia. If insufficient antibody titer is obtained, a tertiary injection of antigen is performed. When a suitable antibody titer develops, a tail vein injection of antigen in saline is administered through a 26 g needle. However, for some antigens, an intraperitoneal injection may be given instead of an intravenous injection. After 3-4 days, the mice are sacrificed and the spleens or lymph nodes is removed and fused with myeloma cells for hybridoma formation.

Example 3

Generation of Diagnostic And Therapeutic Tools

Once an antibody to a desired target is made, such antibody may be conjugated (coupled) with a molecule of choice.

The complete monoclonal antibody may be used or only the Fab fragment. For example, Fab fragments have a number of desirable properties when compared with the intact molecule: equilibrium distribution in extracellular fluid is achieved more rapidly, the volume of distribution is greater, the fragment is eliminated with a far shorter half-life, and is less immunogenic than whole IgG.

The specificity of the aneurysm labeling is assessed by showing the absence of any other fixation but the aneurysm within the vascular tree.

Example 4

Diagnostic Methods And Kits

The present invention also provides in a further aspect a method for detecting an aneurysm in a mammal, the method may comprise for example, administering an antibody or conjugate of the present invention to a mammal having or suspected of having an aneurysm (a cerebral aneurysm or intra-cranial aneurysm). More particularly, the present invention relates to the detection of a cerebral aneurysm (intra-cranial aneurysm) such as for example, an aneurysm of the major brain artery. An exemplary embodiment of a conjugate may include for example, a conjugate comprising an antibody and a label. This conjugate may include a macromolecule or may be coupled to red blood cell (RBC) to be restricted to the vascular compartment.

The method of the present invention may, more specifically be used for the detection of a saccular cerebral artery aneurysm.

The method may comprise intravascularly administering the conjugate to the mammal. Due to the accessibility of subendothelial components in the aneurysm or aneurysm area and the specificity of the antibody moiety of the conjugate, the conjugate may accumulate at the aneurysm site and/or in the aneurysm vicinity directly from the bloodstream.

For diagnostic purpose, a label moiety may be attached to the antibody moiety using techniques readily available to the public. The label moiety may be a radioactive label such as a gamma ray emitting radionuclide: $^{111}$Indium, Technetium-99m, iodine 123 ($^{123}$I), iodine 125 ($^{125}$I). A chelating agent such as dipropylaminetetraacetic acid (DPTA) may be used to associate the radioactive label to the antibody. The label moiety may be a positron emitting radionuclide such as $^{64}$CU or iodine 124 ($^{124}$I). The label moiety may be a near infrared fluorophore (near infrared fluorescent dye) such as Cy7-NHS (Amersham Pharmacia).

In order to be restricted to the blood pool, the conjugate may be bound to a macromolecule such as for example and without limitation, a serum or plasma protein, e.g., albumin, transferrin, globulins; or a synthetic molecule such as dextran, pectin, gelatin, cellulose derivatives. The compound of the present invention may also be bound to a red blood cell (RBC) that confines the conjugate to the vascular compartment.

The label component may be attached to the antibody or to the macromolecule or to the RBC.

Detection of a conjugate accumulated at the aneurysm site and/or in the aneurysm vicinity may be performed according to techniques known in the art and which may vary depending on the characteristic of the label moiety of the conjugate. For example, when the conjugate comprise a gamma ray emitting radionuclide), the aneurysm may be detected by scintigraphy using a gamma camera. Planar images and single photon emission computed tomography (SPECT) images may be obtained. When the conjugate comprises a positron emitting radionuclide, the aneurysm may be detected by positron emission tomography (PET). When the conjugate is a near infrared fluorophore (near infrared fluorescent dye), the aneurysm may be detected by near-infrared imager.

The detection of a signal at the major brain artery site and more particularly, at or near the apex of arterial forks may be indicative of a cerebral aneurysm.

A positive detection of a signal may be followed by an angiography in patients in need thereof.

Follow-up may be performed using the same method of diagnosis to ensure the disappearance or reduction of any intracranial labeling after treatment.

An advantage of cerebral aneurysm detection described herein is that the diagnosis of aneurysm may be performed early, the method is economical and may be applicable for mass detection, it is believed to be reproducible, and non-invasive.

An exemplary embodiment of kits of the present invention may include, for example, a container comprising a labeled antibody, such as for example, an antibody labeled with a radiotracer (a radioactive label having a medical application).

Example 5

Therapeutic Methods And Kits

Once a cerebral aneurysm is detected, it may be treated at once.

The present invention therefore provides in a further aspect a method for treating an aneurysm in a mammal, the method may comprise for example, administering a conjugate of the present invention to a mammal having or suspected of having an aneurysm (a cerebral aneurysm or intra-cranial aneurysm). More particularly, the present invention relates to the treatment of a cerebral aneurysm. Suitable conjugates which may be used for the treatment of a cerebral aneurysm (intra-cranial aneurysm) may comprise, for example, a conjugate which may comprise an antibody moiety and a therapeutic molecule moiety.

The method of the present invention may, more specifically be used for the treatment of a saccular cerebral artery aneurysm.

The method may comprise intravascularly administering the conjugate to the mammal. Due to the accessibility of subendothelial components in the aneurysm or aneurysm area and the specificity of the antibody moiety of the conjugate, the conjugate may accumulate in the aneurysm vicinity and therefore may be used to deliver a therapeutic compound directly from the bloodstream.

An exemplary embodiment of a therapeutic molecule may include for example, but not limited to a compound for inducing thrombosis, a compound for promoting aneurismal wall thickening and/or a compound for promoting cell growth. The therapeutic molecule may, more particularly be selected from the group consisting of a thrombogenic molecule, a polymerisable molecule (intended to clog the aneurysms), a protein (e.g., elastin, fibronectin, or fibrinogen etc), and a cell growth factor (intended to reinforce or make the fundus thicker and stronger). Another exemplary embodiment of a therapeutic molecule may include for example a protease inhibitor, such as an elastase inhibitor or a matrix metallo-proteinase inhibitor. Elastase inhibitors may include, without limitation, alpha-1 antitrypsin, alpha-2 macroglobulin which are the main elastase inhibitors in the serum. Elafin is also a potent inhibitor of elastase and proteinase 3 which is encompassed herewith. Matrix metallo-proteinase inhibitors may include, for example and without limitation tissue inhibitors of metallo-proteinase (TIMPs) or synthetic inhibitors known in the art, such as tetracyclines and tetracycline derivatives such as doxycycline.

The accumulation of the conjugate of the present invention at the aneurysm site and/or in the aneurysm vicinity may allow for the exclusion of the aneurysm from the bloodstream and/or may reduce the risk of its rupture.

Administration of the conjugate may lead for example, to the aneurismal lumen thrombosis or the aneurismal wall thickening.

In order to be restricted to the blood pool, the conjugate may be bound to a macromolecule such as for example and without limitation, a serum or plasma protein, e.g., albumin, transferrin, globulins; or a synthetic molecule such as dextran, pectin, gelatin, cellulose derivatives. The compound of the present invention may also be bound to a red blood cell (RBC) that confines the conjugate to the vascular compartment.

The therapeutic method of the invention may be advantageous when compared to surgical clipping as it may avoids skull opening, brain retraction, ICU therefore, any post-operative complication (brain edema, hydrocephalus, epilepsy or meningitis . . . ). It may also shorten the duration of hospitalization. It may also minimize the occurrence of per-operative rupture. Surgical clipping is illustrated in FIGS. 2(a) and 2(b), showing a right middle cerebral artery (MCA) bifurcation aneurysm, where (20) is the internal carotid artery (ICA), (22) is the superior trunk of segment M2 of the middle cerebral artery (MCA) and (24) represents an aneurysm prior to surgical clipping. Clips (26) are placed at the aneurismal neck (28) then, the fundus resected: To ascertain that the clip is well-seated and that no normal structures are compromised, the fundus should be opened, thrombus (if any) removed, and the fundus resected.

The therapeutic method of the invention may be advantageous when compared to endovascular coiling. For example, it may avoid the risks related to any arterial catheterism. It may avoid the risk of coil embolism, thrombosis or the damage of the supplying artery, dislodgement of the coil or per-operative rupture. Endovascular coiling is illustrated in FIGS. 3(a) to 3(c). A coil (36) is progressively inserted into the aneurysm (34) through the artery (32) and with the help of a catheter (38) until the aneurysm (34) is totally excluded from the bloodstream.

It may be necessary for the patient to be lightly sedated or anesthetized during the diagnostic and/or therapeutic method of the present invention.

An exemplary embodiment of kits of the present invention may include, for example, a container comprising an antibody conjugated with a therapeutic agent.

As used herein, "pharmaceutical composition" means therapeutically effective amounts of the compound(s) together with pharmaceutically acceptable diluents, preservatives, solubilizers, emulsifiers, adjuvant and/or carriers. It may be in the form of liquids or lyophilized or otherwise dried formulations and may include diluents such as water or of various buffer content (e.g., Tris-HCl., acetate, phosphate), pH and ionic strength, additives such as albumin or gelatin to prevent absorption to surfaces, detergents (e.g., Tween 20, Tween 80, Pluronic F68, bile acid salts). For intravascular administration, the pharmaceutical composition is diluted into a pharmaceutically acceptable diluent.

The term "treatment" or "treating" for purposes of the present invention may refer to both therapeutic treatment and prophylactic or preventative measures, wherein the object is to prevent, slow down (lessen) or revert the progression of the disorder (aneurysm). Those in need of treatment include those already with the disorder as well as those prone to have the disorder or those in whom the disorder is to be prevented.

The present description refers to a number of documents, the content of which is herein incorporated by reference in their entirety.

It should be noted that the various components and features of the present invention as described above may be combined in a variety of ways so as to provide other non-illustrated embodiments within the scope of the invention.

It is to be understood that the invention is not limited in its application to the details of construction and parts illustrated in the accompanying drawings and described hereinabove. The invention is capable of other embodiments and of being practiced in various ways. It is also to be understood that the phraseology or terminology used herein is for the purpose of description and not limitation. Hence, although the present invention has been described hereinabove by way of embodiments thereof, it can be modified, without departing from the spirit, scope and nature of the subject invention as described herein.

REFERENCES

The referenced documents listed hereunder are herein incorporated by reference in their entirety.

Molyneux A J, Kerr R S C, Yu L M, Clarke M, Sneade M, Yarnold J A, Sandercock P. International subarachnoid aneurysm trial (ISAT) of neurosurgical clipping versus endovascular coiling in 2143 patients with ruptured intracranial aneurysms: a randomized trial. The Lancet 360: 1267-1274, 2002.

Vega C, Kwoon J V, Lavine S D. Intracranial aneurysms: Current evidence and clinical practice Am Fam Physician. 2002 Aug. 15; 66 (4):601-8

Forbus W D: On the origin of military aneurysms of the superficial cerebral arteries. Bull Johns Hopkins Hosp 1930, 47:239-284

Glynn L E: Medial defects in the circle of Willis and their relation to aneurysm formation. J Pathol Bacteriol 1940 (51): 213-222

Stehbens W E. Histopathology of cerebral aneurysms. Arch Neurol 1963 (8):272-285

Stehbens W E: Intracranial arterial aneurysms, In: Stehbens W E. Pathology of the Cerebral Blood Vessels. Edited by W E Stehbens. St Louis, C V. Mosby, 1972, pp 351-470

Bremer J L. Congenital aneurysms of the cerebral arteries. Arch Pathol 1943 (35): 819-831

Agnoli A L. Vascular anomalies and subarachnoid haemorrhage associated with persisting embryonic vessels. Acta Neuropathol (Wien) 1982 (60):183-199

Sekhar L N, Heros R C. Origin, growth and rupture of saccular aneurysms: A review. Neurosurgery 1981 (8): 248-260

Kojima M, Handa H, Hashimoto N, Kim C, Hazama F. Early changes of experimentally induced cerebral aneurysms in rats: scanning electron microscopic study. Stroke 1988; 19:507-11.

Nagata I, Handa H, Hasimoto N, Hazama F. Experimentally induced cerebral aneurysms in rats: VII. Scanning electron microscope study. Surg Neurol. 1981 October; 16 (4):291-6

Kojima M, Handa H, Hashimoto N, Kim C, Hazama F. Early changes of experimentally induced cerebral aneurysms in rats: scanning electron microscopic study. Stroke 1986; 17:835-41

Greenhill N S, Stehbens W E. Scanning electron-microscope study of the inner surface of experimental aneurysms in rabbits. Atherosclerosis 1982 December 45 (3):319-30

Kim C, Cervos-Navarro J, Kikuchi H, Hashimoto N, Hazama F. Alterations in cerebral vessels in experimental animals and their possible relationship to the development of aneurysms Surg Neurol 1992 November; 38 (5):331-337

Hazama F, Kataoka H, Yamada E, Kayembe K, Hashimoto N, Kojima M, Kim C. Early changes of experimentally induced cerebral aneurysms in rats. Light-microscopic study. Am J Pathol. 1986 September; 124 (3):399-404

Kim C, Kikuchi H, Hashimoto N, Kojima M, Kang Y, Hazama F. Involvement of Internal Elastic Lamina in Development of Induced Cerebral Aneurysms in Rats. Stroke 1988; 19:507-511

Morimoto M, Miyamoto S, Mizoguchi A, Kume N, Kita T, Hashimoto N. Mouse model of cerebral aneurysm: experimental induction by renal hypertension and local hemodynamic changes. Stroke. 2002 July; 33 (7):1911-5

Kondo S, Hashimoto N, Kikuchi H, Hazama F, Nagata I, Kataoka H. Apoptosis of Medial Smooth Muscle cells in the development of Saccular Cerebral Aneurysms in rats. Stroke 1998 (29):181-189

Frosen J, Piippo A, Paetau A, Kangasniemi M, Niemela M, Hernesniemi J, Jaaskelainen J. Remodeling of saccular cerebral artery aneurysm wall is associated with rupture. Stroke 2004 (35):2287-2293

Stehbens W E In Re: Histologic and morphologic comparison of experimental aneurysms with human intracranial aneurysms ANJR 2000 (21):1769-1773

Cawley C M, Dawson R C, Shengelaia G, Bonner G, Barrow D L, Colahan A R T. Arterial saccular aneurysm model in the rabbit. ANJR Am J Neuroradiol 1996 (17):176-1766

Nakatani H, Hashimoto N, Kang Y, Yamazoe N, Kikuchi H, Yamaguchi S, Niimi H. Cerebral blood flow patterns at major vessel bifurcations and aneurysms in rats. J Neurosurg 1991; (74):258-262

Stehbens W E. Etiology of intracranial berry aneurysms. J Neurosurg 1989 (70):823-831

Fukuda S, Hashimoto N, Naritomi H, Nagata I, Nozaki K, Kondo S, Kurino M, Kikuchi H. Prevention of rat cerebral aneurysm formation by inhibition of nitric oxide synthase. Circulation 2000 (101):2532-2538

Houghton A M, Quintero P A, Perkins D L, Kobayashi D K, Kelley D G, Marconcini L A, Mecham R P, Senior R M, Shapiro S D. Elastin fragments drive disease progression in a murine model of emphysema. The Journal of Clinical Investigation 2006 (116):753-759.

Cohen J R, Parikh S, Grella L et al. Neutrophil elastase mRNA transcripts in abdominal aortic aneurysm patients. Surgical forum 1991 (42):358-359

Cajander S, Hassler O. Enzymatic destruction of the elastic lamella at the mouth of cerebral berry aneurysm? An ultrastructural study with special regard to the elastic tissue. Acta Neurol Scand. 1976 March; 53 (3):171-81

Yamada E, Hazama F, Kataoka H, Amano S, Sasahara M, Kayembe K, Katayama K: Elastase-like enzyme in the aorta of spontaneously hypertensive rats. Virchows Arch [Cell Pathol] 1983, 44:241-245

Cohen J R, Sarfati I, Danna D, and Wise L. Smooth muscle cell elastase, atherosclerosis, and abdominal aortic aneurysms. Ann Surg. 1992 September; 216 (3): 327-332

Cohen J R, Keegan L, Sarfati I, Danna D, Ilardi C, Wise L. Neutrophil chemotaxis and neutrophil elastase in the aortic wall in patients with abdominal aortic aneurysms. J Invest Surg. 1991; 4 (4):423-430

Gao Y Z, van Alphen H A, Kamphorst W. Effect of contralateral carotid ligation on experimental carotid artery aneurysm in the rat. Neurol Res. 1991 March; 13 (1):60-4.

Kamphorst W, Gao Y Z, van Alphen H A. Pathological changes in experimental saccular aneurysms in the carotid artery of the rat. Neurol Res. 1991 March; 13 (1):55-9.

Gao Y Z, van Alphen H A, Kamphorst W. Observations on experimental saccular aneurysms in the rat after 2 and 3 months. Neurol Res. 1990 December; 12 (4):260-3.

Van Alphen H A, Gao Y Z, Kamphorst W. An acute experimental model of saccular aneurysms in the rat. Neurol Res. 1990 December; 12 (4):256-9.

Miskolczi L, Guterman L R, Flaherty J D, Hopkins L N. Saccular aneurysm induction by elastase digestion of the arterial wall: a new animal model. Neurosurgery. 1998 September; 43 (3):595-600; discussion 600-1.

Miskolczi L, Guterman L R, Flaherty J D, Szikora I, Hopkins L N. Rapid saccular aneurysm induction by elastase application in vitro. Neurosurgery. 1997 July; 41 (1):220-8; discussion 228-9.

Cajander S, Hassler O. Enzymatic destruction of the elastic lamella at the mouth of cerebral berry aneurysm? An ultrastructural study with special regard to the elastic tissue. Acta Neurol Scand. 1976 March; 53 (3):171-81.

R. O. Weller Subarachnoid haemorrhage and myths about saccular aneurysms. J Clin Pathol. 1995 December; 48 (12): 1078-1081.

Cawley C M, Dawson R C, Shengelaia G, Bonner G, Barrow D L, Colohan A R. Arterial saccular aneurysm model in the rabbit. AJNR Am J Neuroradiol. 1996 October; 17 (9): 1761-6.

Abruzzo T, Shengelaia G G, Dawson R C 3rd, Owens D S, Cawley C M, Gravanis M B. Histologic and morphologic comparison of experimental aneurysms with human intracranial aneurysms. AJNR Am J Neuroradiol. 1998 August; 19 (7):1309-14.

Guglielmi G, Ji C, Massoud T F, Kurata A, Lownie S P, Vinuela F, Robert J. Experimental saccular aneurysms. II. A new model in swine. Neuroradiology. 1994 October; 36 (7):547-50.

Hashimoto T. Flow velocity studies in vein pouch model aneurysms. Neurol Res. 1993 June; 15 (3):185-91.

Young P H, Fischer V W, Guity A, Young P A. Mural repair following obliteration of aneurysms: production of experimental aneurysms. Microsurgery. 1987; 8 (3):128-37.

Hashimoto N, Handa H, Hazama F. Experimentally induced cerebral aneurysms in rats. Surg Neurol. 1978 July; 10 (1):3-8.

Hashimoto N, Handa H, Hazama F. Experimentally induced cerebral aneurysms in rats. Surg Neurol 1978; 10:3-8.

Izumi Nagata, Hajime Handa, Nobuo Hashimoto and Fumitada Hazama. Experimentally induced cerebral aneurysms in rats: VII. Scanning electron microscope study Surgical Neurology Volume 16, Issue 4, October 1981, Pages 291-296

Hazama F, Hashimoto N. Annotation. An animal model of cerebral aneurysms. Neuropathol Appl Neurobiol 1987; 13:77-90.

Hazama F, Kataoka H, Yamada E, Kayembe K, Hashimoto N, Kojima M, Kim C. Early changes of experimentally induced cerebral aneurysms in rats: light-microscopic study. Am J Pathol 1986; 124:399-404.

Kim C, Kikuchi H, Hashimoto N, Hazama F, Kataoka H. Establishment of the experimental conditions for inducing saccular cerebral aneurysms in primates with special reference to hypertension. Acta Neurochir (Wien) 1989; 96:132-6.

Kojima M, Handa H, Hashimoto N, Kim C, Hazama F. Early changes of experimentally induced cerebral aneurysms in rats: scanning electron microscopic study. Stroke 1988; 19:507-11.

Kim C, Kikuchi H, Hashimoto N, Hazama F. Histopathological study of induced cerebral aneurysms in primates. Surg Neurol. 1989 July; 32 (1):45-50.

Hashimoto N, Kim C, Kikuchi H, Kojima M, Kang Y, Hazama F. Experimental induction of cerebral aneurysms in monkeys. J Neurosurg. 1987 December; 67 (6):903-5.

Masafumi Morimoto; Susumu Miyamoto; Akira Mizoguchi; Noriaki Kume; Toru Kita; Nobuo Hashimoto. Mouse Model of Cerebral Aneurysm. Experimental Induction by Renal Hypertension and Local Hemodynamic Changes. Stroke, Jul. 1, 2002; 33 (7): 1911-1915.

Choegon Kim, Jorge Cervos-Navarro, Haruhiko Kikuchi, Nobuo Hashimoto, and Fumitada Hazama. Alterations in Cerebral Vessels in Experimental Animals and Their Possible Relationship to the Development of Aneurysms. Surg Neurol 1992; 38:331-7

Futami K, Yamashita J, Tachibana O, Higashi S, Ikeda K, Yamashima T. Immunohistochemical alterations of fibronectin during the formation and proliferative repair of experimental cerebral aneurysms in rats. Stroke. 1995 September; 26 (9):1659-64.

Kojimahara M, Ooneda G: Ultrastructural observations on bifurcations in rat cerebral arteries. 1. Young and ageing rats. Virchows Arch [B] 1980; 34:21-32.

Takayanagi T, Rennels M L, Nelson E: An electron microscopic study of intimal cushions in intracranial arteries of the cat. Am J Anat 1972; 133:415-30.

Leake D S, Hornebeck W, Brechemier D, Robert L, and Peters T J. Biochim. Biophys. Acta 1983 (761):41-47

Bourdillon M C, Hornebeck W, Soleilhac J M, and Robert L. Biochem Soc Trans 1984 (12):876

Hornebeck W, Brechemier D, Soleilhac J M, Bourdillon M C, and Robert L. in Extracellular Matrix: Structure and Function, ed. Reddi, A H (Liss, N.Y.), vol 25, pp. 269-282

Robert L, Stein F, Pezess M P, Poullain N. Arch Mal Coeur 1967 (60):233-241

Robert L, Robert B, Robert A M Exp Gerontol 1970 (5):339-35.

I claim:

1. A method for detecting an unruptured cerebral aneurysm in a mammal, the method comprising:
   (a) intravascularly administering to the mammal a compound comprising:
      an antibody moiety for binding a protein or cell present in at least one of: a tunica intima, an internal elastic lamina, a tunica media and a tunica adventitia of a cerebral artery, that is accessible to the antibody moiety from the mammal's bloodstream due to formation of gaps between endothelial cells in an unruptured cerebral aneurysm and
      a label moiety;
   (b) detecting in vivo binding at a cerebral artery site of the antibody moiety to a protein or cell that is present in at least one of: a tunica intima, an internal elastic lamina, a tunica media and a tunica adventitia of a cerebral artery, and is accessible to the antibody moiety from the mammal's bloodstream due to formation of gaps between endothelial cells in an unruptured cerebral aneurysm in the mammal,
   wherein the presence of the bound antibody moiety at the cerebral artery site is indicative of an unruptured cerebral aneurysm in the mammal; and
   (c) optionally repeating steps (a) and (b) to ensure disappearance or reduction of any intracranial labeling.

2. The method of claim 1, wherein detecting in vivo binding of the antibody moiety to the protein or cell present in at least one of: a tunica intima, an internal elastic lamina, a tunica media and a tunica adventitia of a cerebral artery, that is accessible to the antibody moiety from the mammal's bloodstream due to formation of gaps between endothelial cells in an unruptured cerebral aneurysm in the mammal is performed by a technique selected from the group consisting of: scintigraphy using a gamma camera, single photon emission computed tomography, positron emission tomography, and near-infrared imaging.

3. The method of claim 1, wherein the label moiety is a radioactive label or a near infrared fluorophore.

4. The method of claim 1, wherein the unruptured cerebral aneurysm is an unruptured saccular cerebral artery aneurysm.

5. A kit for detecting unruptured cerebral aneurysms comprising a container including a pharmaceutically acceptable carrier and a compound coupled to a macromolecule or a red blood cell, said compound comprising: an antibody moiety for binding a protein or cell present in at least one of: a tunica intima, an internal elastic lamina, a tunica media and a tunica adventitia of a cerebral artery, that is accessible to the antibody moiety from the mammal's bloodstream due to formation of gaps between endothelial cells in an unruptured cerebral aneurysm; and a label moiety, wherein the macromolecule comprises albumin, transferrin, a globulin, pectin, gelatin, dextran, or a cellulose derivative.

6. The method of claim 1, wherein the protein or cell is accessible to the antibody moiety from the mammal's bloodstream because of injury to the endothelial cells of the unruptured cerebral aneurysm.

7. The method of claim 6, wherein the protein or cell is a protein selected from the group consisting of: elastin degradation product, elastase, intracellular structural protein, and angiogenic growth factor.

8. The method of claim 7, wherein the angiogenic growth factor is vascular endothelial growth factor (VEGF) or basic fibroblast growth factor (bFGF).

9. The method of claim 1, wherein the protein or cell is a cell surface antigen of a smooth muscle cell or a fibroblast.

10. The method of claim 1, wherein the protein or cell is a glycoprotein.

11. The method of claim 1, wherein the protein or cell is a protein selected from the group consisting of: elastin, fibronectin, fibrinogen, a fibrinogen precursor, collagen, laminin, elastin microfibrillar-associated proteins, desmosine, and isodesmosine.

12. The method of claim 1, wherein the compound is coupled to a red blood cell or a macromolecule having a molecular weight such that the red blood cell or macromolecule confines the compound to the mammal's bloodstream.

13. The method of claim 12, wherein the macromolecule is dextran.

\* \* \* \* \*